United States Patent [19]

Siegel et al.

[11] Patent Number: 5,336,800
[45] Date of Patent: Aug. 9, 1994

[54] MIXED OXAMIDES

[75] Inventors: Bernd Siegel, Ludwigshafen; Manfred Patsch, Wachenheim; Knut Kessel, Mannheim, all of Fed. Rep. of Germany

[73] Assignee: BASF Aktiengesellschaft, Ludwigshafen, Fed. Rep. of Germany

[21] Appl. No.: 295

[22] Filed: Jan. 4, 1993

[30] Foreign Application Priority Data

Jan. 23, 1992 [DE]  Fed. Rep. of Germany ....... 4201669

[51] Int. Cl.$^5$ ................ C07C 305/12; C07C 317/06; C07C 205/06; C07C 205/42; C07C 69/003; C07C 69/12; C07D 241/04
[52] U.S. Cl. ........................... 558/30; 558/29; 558/47; 558/171; 546/1; 546/323; 546/326; 544/386; 544/387; 544/388; 544/390; 544/391; 544/400; 562/52; 562/106; 562/430; 562/432; 564/153; 564/154; 564/159; 560/12; 560/13; 560/39; 560/40; 560/41; 560/42; 560/43; 560/22; 560/129; 560/150; 560/174; 560/169; 560/231
[58] Field of Search ............... 560/251, 129, 169, 174, 560/12, 13, 22, 39, 40, 41, 42, 43, 150, 231; 564/154, 153, 159; 562/430, 52, 432, 106; 558/30, 29, 47, 171; 544/400, 386, 388, 390, 391, 387; 546/1, 323, 326

[56] References Cited

U.S. PATENT DOCUMENTS 5,023,325  6/1991  Tzikas .
5,091,516  2/1992  Siegel et al. .
5,110,808  5/1992  Brittain et al. ................. 514/155
5,241,109  8/1993  Kaschig et al. ................. 562/42

FOREIGN PATENT DOCUMENTS 0210951  2/1987  European Pat. Off. .
0384276  8/1990  European Pat. Off. .
0437699  7/1991  European Pat. Off. .

*Primary Examiner*—Marianne M. Cintins
*Assistant Examiner*—Margaret J. Page
*Attorney, Agent, or Firm*—Oblon, Spivak, McClelland, Maier & Neustadt

[57] ABSTRACT

Oxamides useful as dye intermediates have the formula $$X-Z-\underset{R^1}{N}-CO-CO-\underset{R^2}{N}-L-SO_2-Y$$

where $R^1$ and $R^2$ are independently of each other hydrogen, $C_1$-$C_4$-alkyl or phenyl, X is hydroxyl, nitro or a radical of the formula $-NR^3R^4$, where $R^3$ is hydrogen or $C_1$-$C_4$-alkanoyl and $R^4$ is hydrogen, $C_1$-$C_4$-alkyl or phenyl, Z is $C_2$-$C_8$-alkylene, substituted or unsubstituted phenylene or substituted or unsubstituted naphthylene, or X—Z and $R^1$ are, together with the nitrogen atom joining them together, the radical of the formula

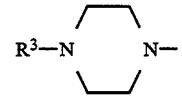

where
$R^3$ is as defined above,
L is a bridge member and
Y is vinyl or a radical of the formula $-C_2H_4-A$, where A is hydroxyl or a group which is detachable under alkaline reaction conditions.

4 Claims, No Drawings

MIXED OXAMIDES

The present invention relates to novel oxamides of the formula I

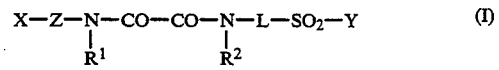 (I)

where

R$^1$ and R$^2$ are independently of each other hydrogen, C$_1$-C$_4$-alkyl or phenyl, X is hydroxyl, nitro or a radical of the formula —NR$^3$R$^4$, where R$^3$ is hydrogen or C$_1$-C$_4$-alkanoyl and R$^4$ is hydrogen, C$_1$-C$_4$-alkyl or phenyl, Z is C$_2$-C$_8$-alkylene, substituted or unsubstituted phenylene or substituted or unsubstituted naphthylene, or X—Z and R$^1$ are, together with the nitrogen atom joining them together, the radical of the formula

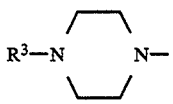

where

R$^3$ is as defined above,

L is C$_2$-C$_8$-alkylene, a radical of the formula

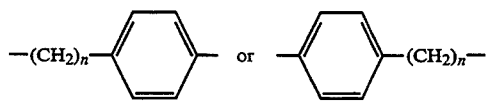

where n is 1 or 2, or substituted or unsubstituted phenylene or naphthylene, and Y is vinyl or a radical of the formula —C$_2$H$_4$—A, where A is hydroxyl or a group which is detachable under alkaline reaction conditions, and to the use thereof as dye intermediates.

It is an object of the present invention to provide novel mixed oxamides that contain unsaturated radicals or precursors thereof and that shall be advantageous for use as fiber-reactive systems of reactive dyes and, if an unsubstituted amino group is additionally present, also as diazo or coupling component.

We have found that this object is achieved by the oxamides of the formula I defined at the beginning.

Any alkyl and alkylene appearing in the above-mentioned formula I may be not only straight-chain but also branched.

Any substituted phenylene or naphthylene appearing in the abovementioned formula I may have as substituents for example C$_1$-C$_4$-alkyl, C$_1$-C$_4$-alkoxy, halogen, carboxyl or hydroxysulfonyl. Substituted phenylene and naphthylene radicals customarily have from one to three substituents.

R$^1$ R$^2$ and R$^4$ are each for example methyl, ethyl, propyl, isopropyl, butyl, isobutyl or sec-butyl.

R$^3$ is for example formyl, acetyl, propionyl, butyryl or isobutyryl.

Z and L are each for example —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH(CH$_3$)—CH$_2$—, —CH(CH$_3$)—CH(CH$_3$)—, 1,2-, 1,3- or 1,4-phenylene, 2- or 3-methyl-1,4-phenylene, 2- or 3-methoxy-1,4-phenylene, 2- or 3-chloro-1,4-phenylene or 2- or 3-hydroxysulfonyl-1,4-phenylene, 2-, 3-, or 4-hydroxysulfonyl-1,3-phenylene, 2,5-dimethyl-1,4-phenylene, 2,6-dimethyl-1,4-phenylene, 2,5-dimethoxy-1,4-phenylene, 2,6-dimethoxy-1,4-phenylene, 2- or 3-carboxyl-1,4-phenylene, or 2- or 4-carboxyl-1,3-phenylene.

L may also be for example 1,4- or 1,8-naphthylene,

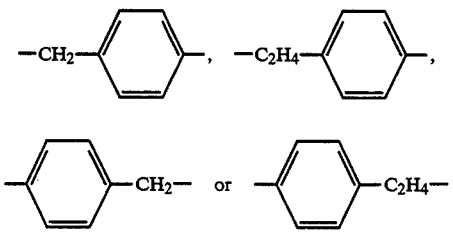

In a —C$_2$H$_4$-A Y in the formula I A may be, inter alia, a group which is detachable under alkaline reaction conditions. Groups of this kind are for example chlorine, OSO$_3$H, SSO$_3$H, OP(O)(OH)$_2$, C$_1$-C$_4$-alkylsulfonyloxy, substituted or unsubstituted phenylsulfonyloxy, C$_1$-C$_4$-alkanoyloxy, C$_1$-C$_4$-dialkylamino, or a radical of the formula

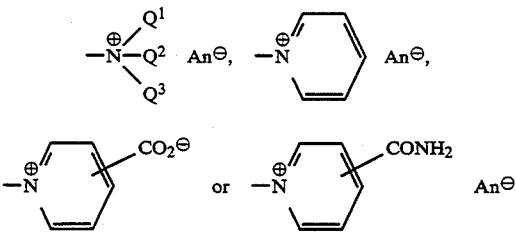

where Q$^1$, Q$^2$ and Q$^3$ are each independently of the others C$_1$-C$_4$-alkyl or benzyl and An$^-$ is in each case the equivalent of an anion. (Suitable anions are for example fluoride, chloride, bromide, iodide, mono-, di- or trichloroacetate, methylsulfonate, phenylsulfonate and 2- or 4-methylphenylsulfonate).

Preference is given to oxamides of the formula I where X is hydroxyl or amino.

Preference is further given to oxamides of the formula I where Z and L are independently of each other phenylene or C$_2$-C$_6$-alkylene.

Preference is further given to oxamides of the formula I where Y is vinyl or a radical of the formula —C$_2$H$_4$—A where A is a group which is detachable under alkaline reaction conditions.

Particular preference is given to oxamides of the formula I where X is amino.

Particular preference is further given to oxamides of the formula I where Z is phenylene.

The oxamides of the invention are obtainable in a conventional manner, for example by reacting in a first step an oxalic acid derivative of the formula II

 (II)

where B$^1$ is C$_1$-C$_4$-alkyl and B$_2$ is C$_1$-C$_4$-alkoxy or halogen, with an amine of the formula III

 (III)

where $X^1$ is hydroxyl, nitro or unsubstituted or $C_1$-$C_4$-alkyl- or phenyl-substituted $C_1$-$C_4$-alkanoylamino and $R^1$ and Z are each as defined above, to form an oxamic ester of the formula IV $$X^1-Z-\underset{R^1}{N}-CO-CO-OB^1 \quad (IV)$$

where $B^1$, $R^1$, $X^1$ and Z are each as defined above.

The second step can then be a reaction with a sulfur-containing amine compound of the formula Va or Vb $$\underset{R^2}{HN-L^1-S-Y} \quad \underset{R^2}{HN-L^2-SO_2-Y}$$

(Va)                  (Vb)

where $L^1$ is $C_2$-$C_8$-alkylene and $L^2$ is a radical of the formula $$-CH_2-\!\!\!\bigcirc\!\!\!-, \quad -\!\!\!\bigcirc\!\!\!-CH_2-$$

substituted or unsubstituted phenylene or naphthylene and $R^2$ and Y are each as defined above, to form an oxamide of the formula (VI) or (Ia)

$$X^1-Z-\underset{R^1}{N}-CO-CO-\underset{R^2}{N}-L^1-S-Y \quad (VI)$$

$$X^1-Z-\underset{R^1}{N}-CO-CO-\underset{R^2}{N}-L^2-SO_2-Y \quad (Ia)$$

where $X^1$, $R^1$, $R^2$, $L^1$, $L^2$, Y and Z are each as defined above.

An oxamide VI is additionally oxidized to convert the thioether to the sulfone of the formula Ib $$X^1-Z-\underset{R^1}{N}-CO-CO-\underset{R^2}{N}-L^1-SO_2-Y \quad (Ib)$$

where $X^1$, $R^1$, $R^2$, $L^1$, Y and Z are each as defined above, for example by means of hydrogen peroxide or hypochlorite.

The compounds of the formula Ia or Ib according to the invention can be converted into amino compounds ($X^1$=amino or $C_1$-$C_4$-alkylamino or phenylamino) either by hydrogenation of the nitro group ($X^1$=nitro) or by deacylation ($X^1$=acylated amino).

It is also possible to reverse the order of the first two reaction steps.

The novel oxamides of the formula I are useful dye intermediates.

In particular, those sulfonyl compounds of the formula Ic $$H_2N-Z-\underset{R^1}{N}-CO-CO-\underset{R^2}{N}-L-SO_2-Y \quad (Ic)$$

where Z is substituted or unsubstituted phenylene or substituted or unsubstituted naphthylene and Y is vinyl or a radical of the formula $-C_2H_4-A$ where A is a group which is detachable under alkaline reaction conditions, and $R^1$, $R^2$ and L are each as defined above, can be used as fiber-reactive system and possibly also as diazo component or coupling component in the synthesis of reactive dyes.

Those sulfonyl compounds of the formula Id $$HO-Z-\underset{R^1}{N}-CO-CO-\underset{R^2}{N}-L-SO_2-Y \quad (Id)$$

where Y is vinyl or a radical of the formula $-C_2H_4-A$, where A is a group which is detachable under alkaline reaction conditions and $R^1$, $R^2$, Z and L are each as defined above, can likewise be used in the synthesis of reactive dyes, in particular as fiber-reactive system.

Embodiments of the invention will now be more particularly described by way of example.

EXAMPLE 1.1

A mixture of 138 g (1 mol) of 3-nitroaniline and 409 g (2.8 mol) of diethyl oxalate was heated to 150°-165° C. and the resulting alcohol was distilled off. After the reaction had ended (check by thin layer chromatography), the reaction mixture was cooled down to room temperature and the resulting precipitate was filtered off with suction and dried to leave 217 g of a compound of the formula

[structure: ethyl N-(3-nitrophenyl)oxamate]

of melting point 153°-157° C. $^1$H NMR ($d_6$-DMSO); δ=1.37 (t, 3H, $CH_3$), 4.37 (q, 2H, $CH_2$), 7.67 (t, 1H, aromatic H), 8.03 (d, 1H, aromatic H), 8.17 (d, 1H, aromatic H), 11.27 (s, 1H, NH) ppm.

EXAMPLE 1.2

138 g (1 mol) of 3-nitroaniline were suspended in 1000 ml of water. To this suspension were added dropwise in the course of 2 hours with vigorous stirring 177.5 g (1.3 mol) of ethyl oxalyl chloride while the pH was maintained at 4-5 with 2N aqueous potassium bicarbonate solution. After the reaction had ended (TLC), the precipitate was filtered off with suction and dried to leave 199 g of the compound described in Example 1.1.

The same method produces the compounds listed in Table 1.

TABLE 1

| Ex. No. | Formula | m.p. |
|---|---|---|
| 1.3 | [structure: 4-methyl-2-nitrophenyl oxamate ethyl ester] | 122-129° C. |

TABLE 1-continued

| Ex. No. | Formula | m.p. |
|---|---|---|
| 1.4 | 4-nitrophenyl NH-C(O)-C(O)-O-C2H5 | 175–180° C. |
| 1.5 | 5-nitro-2-chlorophenyl NH-C(O)-C(O)-O-C2H5 | 105–110° C. |
| 1.6 | 3-nitrophenyl NH-C(O)-C(O)-O-CH3 | |
| 1.7 | 4-nitrophenyl NH-C(O)-C(O)-O-CH3 | |
| 1.8 | 2-(COOH)-4-nitrophenyl NH-C(O)-C(O)-O-C2H5 | |
| 1.9 | 2-(COOH)-5-nitrophenyl NH-C(O)-C(O)-O-C2H5 | |
| 1.10 | 4-SO3H-2-NO2-phenyl NHC(O)C(O)-O-C2H5 | |
| 1.11 | 4-NO2-2-SO3H-phenyl NHC(O)C(O)-O-C2H5 | |
| 1.12 | 2-OH-3-NO2-5-SO3H-phenyl NHC(O)C(O)-O-C2H5 | |
| 1.13 | 3-SO3H-2-OH-5-NO2-phenyl NHC(O)C(O)-O-C2H5 | |

EXAMPLE 2.1

409 g (2.8 mol) of diethyl oxalate and 102 g (1 mol) of 1-acetylamino-2-aminoethane were carefully combined at room temperature and then heated at 90° C. for about 1 hour. After the reaction had ended, the reaction mixture was cooled down, and the precipitate was filtered off with suction, washed with 250 ml of methyl tert-butyl ether and dried to leave 150 g of a compound of the formula

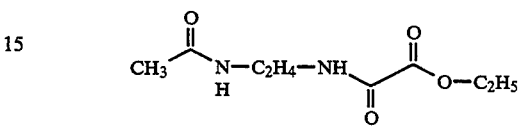

melting point 253°–256° C. $^1$H NMR (d$_6$-DMSO); δ=1.27 (t, 3H, CH$_3$), 1.80 (s, 3H, CH$_3$), 3.17 (m, 4H, CH$_2$—CH$_2$), 4.23 (q, 2H, CH$_2$), 7.93 (t, 1H, NH), 8.93 (t, 1H, NH) ppm.

The method of example 2.1 also produces the compounds listed in Table 2.

TABLE 2

| Ex. No. | Formula |
|---|---|
| 2.2 | CH3-C(O)-NH-C3H6-NH-C(O)-C(O)-O-C2H5 |
| 2.3 | OHC-N(piperazine)N-C(O)-C(O)-O-C2H5 |
| 2.4 | CH3-C(O)-NH-C6H12-NH-C(O)-C(O)-O-C2H5 |
| 2.5 | H3C-C(O)-NH-C2H4-NH-C(O)-C(O)-OCH3 |
| 2.6 | H3C-C(O)-NH-C3H6-NH-C(O)-C(O)-OCH3 |

EXAMPLE 3.1

201 g (1 mol) of 4-aminophenyl 2'-hydroxyethyl sulfone and 292 g (2 mol) of diethyl oxalate were heated at the boil for 9 hours. After the reaction had ended (TLC), the reaction mixture was cooled down, 500 ml of methyl tert-butyl ether were added, and the resulting precipitate was filtered off with suction. Drying left 259 g of a compound of the formula

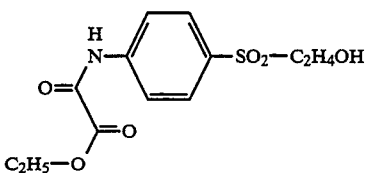

melting point 138°–143° C. $^1$H NMR (d$_6$-DMSO); $\delta = 1.33$ (t, 3H, CH$_3$), 3.43 (m, 2H, CH$_2$), 3.67 (m, 2H, CH$_2$), 4.33 (q, 2H, CH$_2$), 4.70 (t, 1H, OH), 7.88–8.03 (m, 4H, aromatic H), 11.20 (s, 1H, NH) ppm.

EXAMPLE 3.2

100.5 g (0.5 mol) of 4-aminophenyl 2'-hydroxyethyl sulfone were dissolved in 400 ml of tetrahydrofuran, and 50.5 g (0.5 mol) of triethylamine were added. Then a mixture of 75.1 g (0.55 mol) of ethyl oxalyl chloride and 75 ml of tetrahydrofuran was slowly added dropwise at room temperature. To complete the reaction the reaction mixture was then heated at the boil for a further 1.5 hours and then cooled down, the resulting triethylamine hydrochloride was separated off, and the mother liquor was concentrated to about 75 ml. The remaining solids were isolated and dried. This left 121 g of the compound described in Example 3.1.

The same method produces the compounds listed in the following Table 3:

TABLE 3

| Ex. No. | Formula |
|---|---|
| 3.3 | C$_2$H$_5$—O—CO—CO—NH—(3-C$_6$H$_4$)—SO$_2$—C$_2$H$_4$OH |
| 3.4 | C$_2$H$_5$—O—CO—CO—NH—(4-C$_6$H$_4$)—SO$_2$C$_2$H$_4$OH |
| 3.5 | C$_2$H$_5$—O—CO—CO—NH—(naphthyl)—SO$_2$—C$_2$H$_4$OH |
| 3.6 | C$_2$H$_5$O—CO—CO—NH—CH$_2$—(4-C$_6$H$_4$)—SO$_2$—C$_2$H$_4$OH |
| 3.7 | C$_2$H$_5$—O—CO—CO—NH—C$_2$H$_4$—(4-C$_6$H$_4$)—SO$_2$—C$_2$H$_4$OH |
| 3.8 | C$_2$H$_5$—O—CO—CO—NH—(3-C$_6$H$_4$)—CH$_2$—SO$_2$—C$_2$H$_4$OH |
| 3.9 | CH$_3$—O—CO—CO—NH—(4-C$_6$H$_4$)—SO$_2$—C$_2$H$_4$OH |
| 3.10 | CH$_3$—O—CO—CO—NH—(3-C$_6$H$_4$)—SO$_2$—C$_2$H$_4$OH |
| 3.11 | H$_5$C$_2$OCCNH—(4-C$_6$H$_4$)—CH$_2$—SO$_2$—C$_2$H$_4$—OCCH$_3$ |
| 3.12 | H$_5$C$_2$OCCNH—(4-C$_6$H$_4$)—SO$_2$—C$_2$H$_4$—Cl |
| 3.13 | H$_5$C$_2$OCCNH—(4-C$_6$H$_4$)—SO$_2$—C$_2$H$_4$—OCCH$_3$ |
| 3.14 | H$_5$C$_2$OCCNH—(4-C$_6$H$_4$)—CH$_2$—SO$_2$—C$_2$H$_4$—Cl |
| 3.15 | H$_5$C$_2$OCCNH—(3-C$_6$H$_4$)—SO$_2$—C$_2$H$_4$—OCCH$_3$ |
| 3.16 | H$_5$C$_2$OCCNH—(3-C$_6$H$_4$)—SO$_2$—C$_2$H$_4$—Cl |
| 3.17 | H$_5$C$_2$OCCNH—(3-C$_6$H$_4$)—CH$_2$—SO$_2$—C$_2$H$_4$—OCCH$_3$ |
| 3.18 | H$_5$C$_2$OCCNH—(3-C$_6$H$_4$)—CH$_2$—SO$_2$—C$_2$H$_4$—Cl |
| 3.19 | H$_5$C$_2$OCCNH—CH$_2$—(4-C$_6$H$_4$)—SO$_2$—C$_2$H$_4$—Cl |
| 3.20 | H$_5$C$_2$OCCNH—C$_2$H$_4$—(4-C$_6$H$_4$)—SO$_2$—C$_2$H$_4$—Cl |

EXAMPLE 4.1

238 g (1 mol) of the compound described in Example 1.1 were heated together with 123 g (1.02 mol) of 2-aminoethyl 2'-hydroxyethyl sulfide and 1000 ml of toluene at 100° C. for 6 hours. After the reaction had ended (TLC), the reaction mixture was cooled down and the precipitate was filtered off with suction and dried to leave 310 g of a compound of the formula

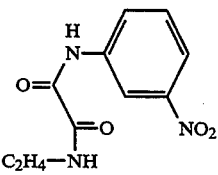
melting point 108°–118° C. $^1$H NMR (d$_6$-DMSO); δ=2.60–2.67 (m, 4H, 2CH$_2$), 3.35–3.60 (m, 4H, 2CH$_2$), 4.87 (t, 1H, OH), 7.65 (t, 1H, aromatic H), 8.02–8.25 (m, 2H, aromatic H), 8.85 (t, 1H, aromatic H), 9.17 (t, 1H, NH), 11.17 (s, 1H, NH) ppm.
The same method produces the compounds listed below in Table 4. (In the case of those compounds with carboxyl or hydroxysulfonyl groups the reaction medium used was not toluene but N,N-dimethylformamide.)
TABLE 4
| Ex. No. | Formula | m.p. |
|---|---|---|
| 4.2 | 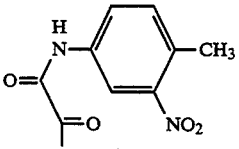 | 133–140° C. |
| 4.3 | 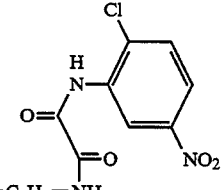 | 119–121° C. |
| 4.4 | 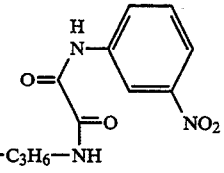 | 110–115° C. |
| 4.5 | 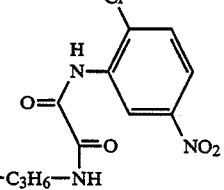 | 160–165° C. |
| 4.6 | 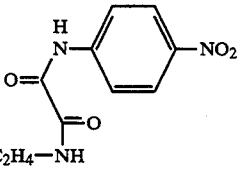 | 143–151° C. |
| 4.7 | 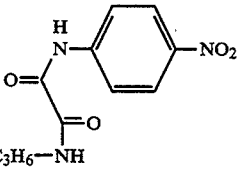 | 138–145° C. |

TABLE 4-continued

| Ex. No. | Formula | m.p. |
|---|---|---|
| 4.8 | HOC$_2$H$_4$—S—C$_2$H$_4$—N(CH$_3$)—CO—CO—NH—(3-NO$_2$-C$_6$H$_4$) | |
| 4.9 | 2-COOH-4-(O$_2$N)-C$_6$H$_3$—NHCONH—C$_2$H$_4$—S—C$_2$H$_4$OH (with central C=O, i.e. NHCOCONH) | |
| 4.10 | 2-COOH-5-(O$_2$N)-C$_6$H$_3$—NHCOCONH—C$_2$H$_4$—S—C$_2$H$_4$OH | |
| 4.11 | 4-HO$_3$S-2-NO$_2$-C$_6$H$_3$—NHCOCONH—C$_2$H$_4$—S—C$_2$H$_4$OH | |
| 4.12 | 4-O$_2$N-2-SO$_3$H-C$_6$H$_3$—NHCOCONH—C$_2$H$_4$—S—C$_2$H$_4$OH | |
| 4.13 | 2-OH-3-O$_2$N-5-SO$_3$H-C$_6$H$_2$—NHCOCONH—C$_2$H$_4$—S—C$_2$H$_4$OH | |
| 4.14 | 2-OH-3-SO$_3$H-5-O$_2$N-C$_6$H$_2$—NHCOCONH—C$_2$H$_4$—S—C$_2$H$_4$OH (with NH attached on the remaining position) | |
| 4.15 | 2-OH-3-O$_2$N-5-SO$_3$H-C$_6$H$_2$—NH—COCO—NH—C$_3$H$_6$—S—C$_2$H$_4$OH | |

EXAMPLE 5.1

202 g (1 mol) of the compound described in Example 2.1 were heated together with 201 g (1 mol) of 3-aminophenyl 2-hydroxyethyl sulfone in 500 ml of N,N-dimethylformamide at 100° C. for 7 hours. After the reaction had ended, the solvent was substantially stripped off and the residue was suspended in 1000 ml of water. The resulting precipitate was filtered off with suction and dried to leave 303 g of a compound of the formula

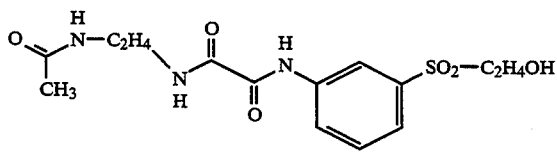

melting point 177°–181° C. $^1$H NMR (d$_6$-DMSO); δ=1.88 (s, 3H, CH$_3$), 3.30 (m, 2H, CH$_2$), 3.35 (m, 2H, CH$_2$), 3.50 (t, 2H, CH$_2$), 3.78 (t, 2H, CH$_2$), 3.97 (s, 1H, OH), 7.65–7.73 (m, 2H, aromatic H), 8.03 (t, 1H, NH), 8.17 (d, 1H, aromatic H), 8.55 (s, 1H, aromatic H), 9.05 (t, 1H, NH), 11.00 (s, 1H, NH) ppm.

EXAMPLE 5.2

102 g (1 mol) of 1-acetylamino-2-aminoethane and 301 g (1 mol) of the compound described in Example 3.3 were heated in 500 ml of N,N-dimethylformamide at 100° C. for 7 hours. After the reaction had ended (TLC), the solvent was substantially stripped off and 500 ml of water were added to the residue. The resulting precipitate was filtered off with suction and dried to leave 300 g of the compound described in Example 5.1.

The same method produces the compounds listed below in Table 5.

TABLE 5

| Ex. No. | Formula |
|---|---|
| 5.3 | H$_3$CCONH—C$_2$H$_4$—NHCCNH—CH$_2$—⟨phenyl⟩—SO$_2$—C$_2$H$_4$OH |
| 5.4 | H$_3$CCONH—C$_2$H$_4$—NHCCNH—C$_2$H$_4$—⟨phenyl⟩—SO$_2$—C$_2$H$_4$OH |
| 5.5 | H$_3$CCONH—C$_2$H$_4$—NHCCNH—⟨naphthyl⟩—SO$_2$—C$_2$H$_4$OH |
| 5.6 | H$_3$CCONH—C$_2$H$_4$—NHCCNH—⟨phenyl⟩—CH$_2$—SO$_2$C$_2$H$_4$OH |
| 5.7 | H$_3$CCONH—C$_2$H$_4$—NHCCNH—⟨phenyl⟩—SO$_2$—C$_2$H$_4$OH |
| 5.8 | H$_3$CCONH—C$_3$H$_6$—NHCCNH—⟨phenyl⟩—SO$_2$—C$_2$H$_4$OH |
| 5.9 | H$_3$CCONH—C$_3$H$_6$—NHCCNH—⟨phenyl⟩—SO$_2$—C$_2$H$_4$OH |
| 5.10 | H$_3$CCONH—C$_3$H$_6$—NHCCNH—CH$_2$—⟨phenyl⟩—SO$_2$—C$_2$H$_4$OH |
| 5.11 | H$_3$CCONH—C$_3$H$_6$—NHCC—NH—⟨naphthyl⟩—SO$_2$—C$_2$H$_4$OH |
| 5.12 | H$_3$CCONH—C$_3$H$_6$—NHCC—NH—⟨phenyl⟩—CH$_2$—SO$_2$H$_4$OH |

TABLE 5-continued

| Ex. No. | Formula |
|---|---|
| 5.13 | H₃CCONH—C₃H₆—NHCONHCONH—C₂H₄—C₆H₄—SO₂—C₂H₄OH |
| 5.14 | OHC—N(piperazine)N—CO—CO—NH—C₆H₄—SO₂—C₂H₄OH (meta) |
| 5.15 | OHC—N(piperazine)N—CO—CO—NH—C₆H₄—SO₂—C₂H₄OH (para) |
| 5.16 | OHC—N(piperazine)N—CO—CO—NH—CH₂—C₆H₄—SO₂—C₂H₄OH |
| 5.17 | OHC—N(piperazine)N—CO—CO—NH—C₂H₄—C₆H₄—SO₂—C₂H₄OH |
| 5.18 | OHC—N(piperazine)N—CO—CO—NH—(naphthalene)—SO₂—C₂H₄OH |
| 5.19 | OHC—N(piperazine)N—CO—CO—NH—C₆H₄—CH₂—SO₂—C₂H₄OH |

EXAMPLE 6.1

238 g (1 mol) of the compound described in Example 1.1 and 201 g (1 mol) of 3-aminophenyl 2′-hydroxyethyl sulfone were heated in 500 ml of N,N-dimethylformamide at 100° C. for 7 hours. After the reaction had ended (TLC), the solvent was substantially stripped off and 500 ml of water were added to the residue. The resulting precipitate was filtered off with suction and dried to leave 334 g of a compound of the formula

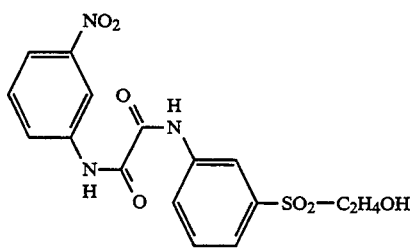

$^1$H NMR (d$_6$-DMSO); Δ=3.48 (t, 2H, CH$_2$), 3.77 (t, 2H, CH$_2$), 4.65 (s, 1H, OH), 7.73 (m, 3H, aromatic H), 8.03–8.32 (m, 3H, aromatic H), 8.58 (s, 1H, aromatic H), 8.92 (s, 1H, aromatic H), 11.32 (s, 1H, NH), 11.42 (s, 1H, NH) ppm.

EXAMPLE 6.2

138 g (1 mol) of 3-nitroaniline were heated together with 301 g (1 mol) of the compound described in Example 3.3 in 500 ml of N,N-dimethylformamide at 100° C. for 7 hours. After the reaction had ended (TLC), the solvent was substantially stripped off and the residue was diluted with 500 ml of water. The resulting precipitate was filtered off with suction, washed and dried to leave 330 g of the compound described in Example 6.1.

The same method produces the compounds listed below in Table 6.

TABLE 6

| Ex. No. | Formula |
|---|---|
| 6.3 | 4-O₂N-C₆H₄-NHC(O)C(O)NH-C₆H₄-3-SO₂-C₂H₄OH |
| 6.4 | 3-O₂N-C₆H₄-NHC(O)C(O)NH-C₆H₄-4-SO₂-C₂H₄OH |
| 6.5 | (3-NO₂, 4-CH₃-C₆H₃)-NHC(O)C(O)NH-C₆H₄-3-SO₂-C₂H₄OH |
| 6.6 | (4-NO₂, 2-Cl-C₆H₃)-NHC(O)C(O)NH-C₆H₄-4-SO₂-C₂H₄OH |
| 6.7 | (4-NO₂, 2-Cl-C₆H₃)-NHC(O)C(O)NH-C₆H₄-3-SO₂-C₂H₄OH |
| 6.8 | (3-NO₂, 4-CH₃-C₆H₃)-NHC(O)C(O)NH-C₆H₄-4-SO₂-C₂H₄OH |
| 6.9 | 3-O₂N-C₆H₄-NHC(O)C(O)NH-C₆H₄-4-CH₂-SO₂-C₂H₄OH |
| 6.10 | 4-O₂N-C₆H₄-NHC(O)C(O)NH-C₆H₄-4-CH₂-SO₂-C₂H₄OH |
| 6.11 | 3-O₂N-C₆H₄-NHC(O)C(O)NH-(naphthyl)-SO₂-C₂H₄OH |
| 6.12 | 4-O₂N-C₆H₄-NHC(O)C(O)NH-(naphthyl)-SO₂-C₂H₄OH |
| 6.13 | 3-O₂N-C₆H₄-NHC(O)C(O)NH-CH₂-C₆H₄-4-SO₂-C₂H₄OH |

TABLE 6-continued

| Ex. No. | Formula |
|---|---|
| 6.14 | $O_2N$-C$_6$H$_4$-HNCOCHN-CH$_2$-C$_6$H$_4$-SO$_2$-C$_2$H$_4$OH (with C=O) |
| 6.15 | 3-$O_2N$-C$_6$H$_4$-NHCOCONH-CH$_2$-CH$_2$-C$_6$H$_4$-SO$_2$-C$_2$H$_4$OH |
| 6.16 | 4-$O_2N$-C$_6$H$_4$-HNCOCHN-CH$_2$-CH$_2$-C$_6$H$_4$-SO$_2$-C$_2$H$_4$OH |
| 6.17 | 2-COOH, 5-$O_2N$-C$_6$H$_3$-NHCOCONH-C$_6$H$_4$-SO$_2$-C$_2$H$_4$OH |
| 6.18 | 2-COOH, 5-$O_2N$-C$_6$H$_3$-NHCOCONH-C$_6$H$_4$(3-SO$_2$-C$_2$H$_4$OH) |
| 6.19 | 2-OH, 3-$O_2N$, 5-SO$_3$H-C$_6$H$_2$-NHCOCONH-C$_6$H$_4$-SO$_2$-C$_2$H$_4$OH |
| 6.20 | 2-OH, 3-$O_2N$, 5-SO$_3$H-C$_6$H$_2$-NHCOCONH-C$_6$H$_4$(3-SO$_2$-C$_2$H$_4$OH) |

EXAMPLE 7.1

202 g (1 mol) of the compound described in Example 2.1 were heated with 121 g (1 mol) of 2-aminoethyl 2'-hydroxyethyl sulfide in 1000 ml of tetrahydrofuran at the boil for 5 hours. The reaction mixture was then cooled down to about 10° C. and the resulting precipitate was filtered off with suction to leave 240 g of a compound of the formula

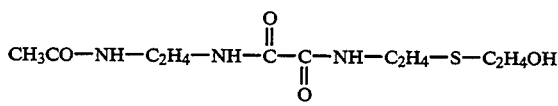

$CH_3CO-NH-C_2H_4-NH-\overset{O}{\underset{\parallel}{C}}-C-NH-C_2H_4-S-C_2H_4OH$ $^1$NMR (d$_6$-DMSO); δ=1.80 (s, 3H, CH$_3$), 2.60 (m, 4H, CH$_2$), 3.18 (m, 4H, CH$_2$), 3.32 (m, 2H, CH$_2$), 3.55 (t, 2H, CH$_2$), 4.75 (S, 1H, OH), 7.97 (t, 1H, NH), 8.80 (t, 1H, NH), 8.87 (t, 1H, NH) ppm.

The same method gives the compounds listed below in Table 7.

TABLE 7

| Ex. No. | Formula |
|---|---|
| 7.2 | $H_3CHN-C_3H_6-NHCOCONH-C_2H_4-S-C_2H_4OH$ (with two C=O) |
| 7.3 | OHC-N(piperazine)N-COCO-NH-C$_2$H$_4$-S-C$_2$H$_4$OH |
| 7.4 | $H_3CNH-C_6H_{12}-NHCOCONH-C_2H_4-S-C_2H_4OH$ |
| 7.5 | $H_3CNH-C_6H_{12}-NHCOCONH-C_2H_4-S-C_2H_4OH$ |

TABLE 7-continued

| Ex. No. | Formula |
|---|---|
| 7.6 | H₃CNH—C₂H₄—NHCCNH—C₃H₆—S—C₂H₄OH (with two C=O groups) |
| 7.7 | H₃CCNH—C₃H₆—NHCCNH—C₃H₆—S—C₂H₄OH (with two C=O groups) |
| 7.8 | OHC—N(piperazine)N—C(=O)—C(=O)—NH—C₃H₆—S—C₂H₄OH |
| 7.9 | H₃CCNH—C₆H₁₂—NHCCNH—C₃H₆—S—C₂H₄OH (with two C=O groups) |

EXAMPLE 8.1

313 g (1 mol) of the compound described in Example 4.1 were suspended in 2000 ml of water, 2.8 g of Na₂WO₄×2H₂O were added, and the mixture was heated to 90°–95° C. 340 g (3 mol) of 30% by weight aqueous hydrogen peroxide were then added dropwise at such a rate that it was possible to maintain the reaction mixture under a gentle boil. On completion of the addition the mixture was stirred at 90°–95° C. for 4 hours and then cooled down, and the resulting precipitate was separated off and washed peroxide-free. This left 397 g of a compound of the formula

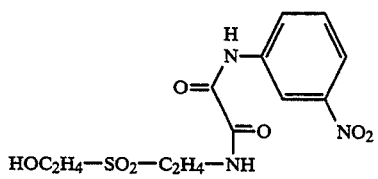

¹H NMR (d₆-DMSO); δ=3.37 (t, 2H, CH₂), 3.52 (t, 2H, CH₂), 3.77 (m, 2H, CH₂), 3.95 (m, 2H, CH₂), 5.10 (s, 1H, OH), 7.68 (t, 1H, aromatic H), 8.00 (d, 1H, aromatic H), 8.25 (d, 1H, aromatic H), 8.85 (s, 1H aromatic H), 9.07 (t, 1H, NH), 11.07 (s, 1H, NH)ppm.

The same method produces the compounds listed below in Table 8.

TABLE 8

| Ex. No. | Formula |
|---|---|
| 8.2 | O₂N—(3-nitrophenyl)—NHCCNH—C₃H₆—SO₂—C₂H₄OH |
| 8.3 | O₂N—(phenyl with Cl)—NHCCNH—C₂H₄—SO₂—C₂H₄OH |
| 8.4 | O₂N—(phenyl with H₃C)—NHCCNH—C₂H₄—SO₂—C₂H₄OH |
| 8.5 | O₂N—(4-nitrophenyl)—NHCCNH—C₂H₄—SO₂—C₂H₄OH |
| 8.6 | O₂N—(4-nitrophenyl)—NHCCNH—C₃H₆—SO₂—C₂H₄OH |
| 8.7 | O₂N—(phenyl with Cl)—NHCCNH—C₃H₆—SO₂—C₂H₄OH |
| 8.8 | O₂N—(phenyl with H₃C)—NHCCNH—C₃H₆—SO₂—C₂H₄OH |

TABLE 8-continued

| Ex. No. | Formula |
|---|---|
| 8.9 | $O_2N-C_6H_4-NHCOCON(CH_3)-C_2H_4-SO_2-C_2H_4OH$ (3-nitrophenyl) |
| 8.10 | $H_3CCONH-C_3H_6-NHCOCONH-C_2H_4-SO_2-C_2H_4OH$ |
| 8.11 | $OHC-N(\text{piperazine})N-COCO-NH-C_2H_4-SO_2-C_2H_4OH$ |
| 8.12 | $H_3CCONH-C_6H_{12}-NHCOCONH-C_2H_4-SO_2-C_2H_4OH$ |
| 8.13 | $H_3CCONH-C_2H_4-NHCOCONH-C_3H_6-SO_2-C_2H_4OH$ |
| 8.14 | $H_3CCONH-C_3H_6-NHCOCONH-C_3H_6-SO_2-C_2H_4OH$ |
| 8.15 | $OHC-N(\text{piperazine})N-COCO-NH-C_3H_6-SO_2-C_2H_4OH$ |
| 8.16 | $H_3CCO-NH-C_6H_{12}-NHCOCONH-C_3H_6-SO_2-C_2H_4OH$ |
| 8.17 | 2-COOH, 4-$O_2N$-phenyl-NHCONH-$C_2H_4$-SO$_2$-$C_2H_4$OH |
| 8.18 | 2-COOH, 5-$O_2N$-phenyl-NHCONH-$C_2H_4$-SO$_2$-$C_2H_4$OH |
| 8.19 | 2-OH, 3-$O_2N$, 5-SO$_3$H-phenyl-NHCONH-$C_2H_4$-SO$_2$-$C_2H_4$OH |

TABLE 8-continued

| Ex. No. | Formula |
| --- | --- |
| 8.20 | 3-sulfo-6-hydroxy-5-nitro substituted benzene with $NHCONH-C_2H_4-SO_2-C_2H_4OH$ group; $SO_3H$ at top, $OH$ ortho, $O_2N$ para to $OH$ |

8.20: Structure — benzene ring with $SO_3H$, $OH$, $O_2N$, and $NHCCNH-C_2H_4-SO_2-C_2H_4OH$ (urea linkage with two C=O) substituents.

EXAMPLE 9.1

34.5 g (0.1 mol) of the compound described in Example 8.1 were introduced into 100 ml of acetic anhydride and heated at 90°–95° C. for 1 hour. After the reaction had ended (TLC), excess anhydride was carefully destroyed with 100 ml of water, the mixture was cooled down, and the resulting precipitate was filtered off with suction at room temperature to leave 36.8 g of a compound of the formula $O_2N$—C$_6$H$_4$—$NHCCNH-C_2H_4-SO_2-C_2H_4-OCCH_3$ (with two C=O in urea and one in acetate)

$^1$H NMR (d$_6$-DMSO); δ=2.07 (s, 3H, CH$_3$), 3.45 (t, 2H, CH$_2$), 3.60 (t, 2H, CH$_2$), 3.70 (m, 2H, CH$_2$), 4.37 (t, 2H, CH$_2$), 7.67 (t, 1H, aromatic H), 8.00 (d, 1H, aromatic H), 8.25 (d, 1H, aromatic H), 8.86 (t, 1H, aromatic H), 9.27 (t, 1H, NH), 11.85 (s, 1H, NH) ppm.

The same method produces the compounds listed below in Table 9.

TABLE 9

| Ex. No. | Formula |
| --- | --- |
| 9.2 | 3-$O_2N$-C$_6$H$_4$-NHCCNH-C$_3$H$_6$-SO$_2$-C$_2$H$_4$-OCCH$_3$ |
| 9.3 | 4-$O_2N$-C$_6$H$_4$-NHCCNH-C$_2$H$_4$-SO$_2$-C$_2$H$_4$-OCCH$_3$ |
| 9.4 | 4-$O_2N$-C$_6$H$_4$-NHCCNH-C$_3$H$_6$-SO$_2$-C$_2$H$_4$-OCCH$_3$ |
| 9.5 | 3-$O_2N$-C$_6$H$_4$-NHCC-N(CH$_3$)-C$_2$H$_4$-SO$_2$-C$_2$H$_4$-OCCH$_3$ |
| 9.6 | 3-$O_2N$-4-CH$_3$-C$_6$H$_3$-NHCCNH-C$_2$H$_4$-SO$_2$-C$_2$H$_4$-OCCH$_3$ |
| 9.7 | 3-$O_2N$-4-CH$_3$-C$_6$H$_3$-NHCCNH-C$_3$H$_6$-SO$_2$-C$_2$H$_4$-OCCH$_3$ |
| 9.8 | 4-$O_2N$-2-Cl-C$_6$H$_3$-NHCCNH-C$_2$H$_4$-SO$_2$-C$_2$H$_4$-OCCH$_3$ |

TABLE 9-continued

| Ex. No. | Formula |
|---|---|
| 9.9 | 2-chloro-5-nitrophenyl connected to $NHCONHCO-C_3H_6-SO_2-C_2H_4-OCOCH_3$ (phenyl ring has $O_2N$ at 5-position and $Cl$ at 2-position) |
| 9.10 | $O_2N$-phenyl-$NHCONHCO-CH_2$-phenyl-$SO_2-C_2H_4-OCOCH_3$ (3-nitro) |
| 9.11 | $O_2N$-phenyl-$NHCONHCO-C_2H_4$-phenyl-$SO_2-C_2H_4-OCOCH_3$ (3-nitro) |
| 9.12 | $O_2N$-phenyl-$NHCONHCO$-phenyl-$CH_2-SO_2-C_2H_4-OCOCH_3$ (3-nitro) |
| 9.13 | $O_2N$-phenyl-$NHCONHCO-CH_2$-phenyl-$SO_2-C_2H_4-OCOCH_3$ (4-nitro) |
| 9.14 | $O_2N$-phenyl-$NHCONHCO-C_2H_4$-phenyl-$SO_2-C_2H_4-OCOCH_3$ (4-nitro) |
| 9.15 | $O_2N$-phenyl-$NHCONHCO$-phenyl-$CH_2-SO_2-C_2H_4-OCOCH_3$ (4-nitro) |

EXAMPLE 10.1

36.6 g (0.095 mol) of the compound described in Example 9.1 were admixed with 300 ml of 70% by weight ethanol and 1 g of palladium on carbon (10% by weight) and hydrogenated at 40° to 50° C. After the absorption of hydrogen had ceased, the reaction mixture was heated to the boil and filtered hot to remove the catalyst, and the filtrate was cooled down to about 15° C. The resulting precipitate was separated off and dried to leave 30.4 g of a compound of the formula $H_2N$-phenyl-$NHCONHCO-C_2H_4-SO_2-C_2H_4-OCOCH_3$ (3-amino)

$^1$H NMR (d$_6$-DMSO); δ=2.08 (s, 3H, CH$_3$), 3.05 (t, 2H, CH$_2$), 3.58 (t, 2H, CH$_2$), 3.75 (m, 2H, CH$_2$), 4.41 (t, 2H, CH$_2$), 5.07 (s, 2H, NH$_2$), 6.45 (d, 1H, aromatic H), 6.95–7.07 (m, 2H aromatic H), 7.16 (s, 1H, aromatic H), 9.12 (t, $^1$H, NH), 10.22 (s, 1H, NH) ppm.

The same method produces the compounds listed below in Table 10.

TABLE 10

| Ex. No. | Formula |
|---|---|
| 10.2 | $H_2N$-phenyl-$NHCONHCO-C_3H_6-SO_2-C_2H_4-OCOCH_3$ |

TABLE 10-continued

| Ex. No. | Formula |
|---|---|
| 10.3 | $H_2N-C_6H_4-NHC(O)C(O)NH-C_2H_4-SO_2-C_2H_4-OC(O)CH_3$ |
| 10.4 | $H_2N-C_6H_4-NHC(O)C(O)NH-C_3H_6-SO_2-C_2H_4-OC(O)CH_3$ |
| 10.5 | 3-$H_2N-C_6H_4-NHC(O)C(O)-N(CH_3)-C_2H_4-SO_2-C_2H_4-OC(O)CH_3$ |
| 10.6 | 3-amino-4-methylphenyl-NHC(O)C(O)NH-C_2H_4-SO_2-C_2H_4-OC(O)CH_3 |
| 10.7 | 3-amino-4-methylphenyl-NHC(O)C(O)NH-C_3H_6-SO_2-C_2H_4-OC(O)CH_3 |
| 10.8 | 5-amino-2-chlorophenyl-NHC(O)C(O)NH-C_2H_4-SO_2-C_2H_4-OC(O)CH_3 |
| 10.9 | 5-amino-2-chlorophenyl-NHC(O)C(O)NH-C_3H_6-SO_2-C_2H_4-OC(O)CH_3 |
| 10.10 | 3-$H_2N-C_6H_4-NHC(O)C(O)NH-CH_2-C_6H_4-SO_2-C_2H_4-OC(O)CH_3$ |
| 10.11 | 3-$H_2N-C_6H_4-NHC(O)C(O)NH-C_2H_4-C_6H_4-SO_2-C_2H_4-OC(O)CH_3$ |
| 10.12 | 3-$H_2N-C_6H_4-NHC(O)C(O)NH-C_6H_4-CH_2-SO_2-C_2H_4-OC(O)CH_3$ |
| 11.13 | 4-$H_2N-C_6H_4-NHC(O)C(O)NH-CH_2-C_6H_4-SO_2-C_2H_4-OC(O)CH_3$ |

TABLE 10-continued

| Ex. No. | Formula |
|---|---|
| 11.14 | H₂N—⟨C₆H₄⟩—NHCCNH—C₂H₄—⟨C₆H₄⟩—SO₂—C₂H₄—OCCH₃ (with two C=O groups on urea and one C=O on acetate) |
| 11.15 | H₂N—⟨C₆H₄⟩—NHCCNH—⟨C₆H₄⟩—CH₂—SO₂—C₂H₄—OCCH₃ |

EXAMPLE 11.1

345 g (1 mol) of the compound described in Example 8.1 were suspended in 1000 ml of methanol, admixed with 15 g of Raney nickel and 5 ml of propionic acid and hydrogenated at 50° C. and a hydrogen pressure of 1–3 bar. After the absorption of hydrogen had ceased, the catalyst was removed by filtration, the solvent was substantially stripped off, and the remaining residue was isolated to leave 268 g of a compound of the formula

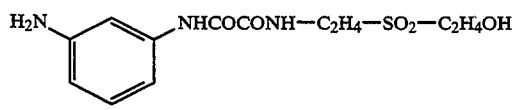

$^1$H NMR (d$_6$-DMSO); δ=3.33 (t, 2H, CH$_2$), 3.42 (t, 2H, CH$_2$, 3.65 (q, 2H, CH$_2$), 3.82 (q, 2H, CH$_2$), 5.17 (s, 2H, NH$_2$), 5.20 (t, 1H, OH), 6.33 (d, 1H, aromatic H), 6.85–7.00 (m, 2H, aromatic H), 7.10 (s, 1H, aromatic H), 9.07 (t, 1H, NH), 10.25 (s, 1H, NH) ppm.

The same method produces the compounds listed below in Table 11.

TABLE 11

| Ex. No. | Formula |
|---|---|
| 11.2 | H₂N—⟨C₆H₄⟩—NHCOCONH—C₃H₆—SO₂—C₂H₄OH |
| 11.3 | H₂N—⟨C₆H₃(Cl)⟩—NHCCNH—C₂H₄—SO₂—C₂H₄OH |
| 11.4 | H₂N—⟨C₆H₃(CH₃)⟩—NHCCNH—C₂H₄—SO₂—C₂H₄OH |
| 11.5 | H₂N—⟨C₆H₄⟩—NHCCNH—C₂H₄—SO₂—C₂H₄OH |
| 11.6 | H₂N—⟨C₆H₄⟩—NHCCNH—C₃H₆—SO₂—C₂H₄OH |
| 11.7 | H₂N—⟨C₆H₃(Cl)⟩—NHCCNH—C₃H₆—SO₂—C₂H₄OH |
| 11.8 | H₂N—⟨C₆H₃(CH₃)⟩—NHCCNH—C₃H₆—SO₂—C₂H₄OH |
| 11.9 | H₂N—⟨C₆H₄⟩—NHCC—N(CH₃)—C₂H₄—SO₂—C₂H₄OH |
| 11.10 | H₂N—⟨C₆H₄⟩—NHCC—NH—⟨C₆H₄⟩—SO₂—C₂H₄OH |
| 11.11 | H₂N—⟨C₆H₄⟩—NHCCNH—⟨C₆H₄⟩—SO₂—C₂H₄OH |
| 11.12 | H₂N—⟨C₆H₃(CH₃)⟩—NHCCNH—⟨C₆H₄⟩—SO₂—C₂H₄OH |
| 11.13 | H₂N—⟨C₆H₃(Cl)⟩—NHCCNH—⟨C₆H₄⟩—SO₂—C₂H₄OH |
| 11.14 | H₂N—⟨C₆H₃(Cl)⟩—NHCC—NH—⟨C₆H₄⟩—SO₂—C₂H₄OH |
| 11.15 | H₂N—⟨C₆H₃(CH₃)⟩—NHCCNH—⟨C₆H₄⟩—SO₂—C₂H₄OH |
| 11.16 | H₂N—⟨C₆H₄⟩—NHCCNH—⟨C₆H₄⟩—CH₂—SO₂—C₂H₄OH |
| 11.17 | H₂N—⟨C₆H₄⟩—NHCCNH—⟨C₆H₄⟩—CH₂—SO₂—C₂H₄OH |

TABLE 11-continued

| Ex. No. | Formula |
|---|---|
| 11.18 | H₂N–C₆H₄–NHCONH–naphthyl–SO₂–C₂H₄OH (3-amino) |
| 11.19 | H₂N–C₆H₄–NHCONH–naphthyl–SO₂–C₂H₄OH (4-amino) |
| 11.20 | H₂N–C₆H₄–NHCONH–CH₂–C₆H₄–SO₂–C₂H₄OH (3-amino) |
| 11.21 | H₂N–C₆H₄–NHCONH–CH₂–C₆H₄–SO₂–C₂H₄OH (4-amino) |
| 11.22 | H₂N–C₆H₄–NHCONH–C₂H₄–C₆H₄–SO₂–C₂H₄OH (3-amino) |
| 11.23 | H₂N–C₆H₄–NHCONH–C₂H₄–C₆H₄–SO₂–C₂H₄OH (4-amino) |
| 11.24 | 2-COOH, 4-NH₂–C₆H₃–NHCONH–C₂H₄–SO₂–C₂H₄OH |
| 11.25 | 2-COOH, 5-NH₂–C₆H₃–NHCONH–C₂H₄–SO₂–C₂H₄OH |
| 11.26 | 3-NH₂, 2-OH–C₆H₃–NHCONH–C₂H₄–SO₂–C₂H₄OH (5-SO₃H) |
| 11.27 | 5-NH₂, 2-OH, 3-HO₃S–C₆H₂–NHCONH–C₂H₄–SO₂–C₂H₄OH |
| 11.28 | 3-NH₂, 2-OH, 5-SO₃H–C₆H₂–NHCONH–C₃H₆–SO₂–C₂H₄OH |
| 11.29 | 2-COOH, 5-NH₂–C₆H₃–NHCONH–C₆H₄–SO₂–C₂H₄OH (4-) |
| 11.30 | 2-COOH, 5-NH₂–C₆H₃–NHCONH–C₆H₄–SO₂–C₂H₄OH (3-) |
| 11.31 | 3-NH₂, 2-OH, 5-SO₃H–C₆H₂–NHCONH–C₆H₄–SO₂–C₂H₄OH (4-) |
| 11.32 | 3-NH₂, 2-OH, 5-SO₃H–C₆H₂–NHCONH–C₆H₄–SO₂–C₂H₄OH (3-) |

EXAMPLE 12.1

357 g (1 mol) of the compound described in Example 5.1 were heated at the boil in 500 ml of 10% by weight hydrochloric acid for 5 hours. The reaction mixture was then substantially concentrated, and the remaining residue was filtered off with suction and dried to leave 236 g of a compound of the formula HCl × H₂N–C₂H₄–NHCONH–C₆H₄–SO₂–C₂H₄OH (3-)

¹H NMR (d₆-DMSO); δ=3.01 (t, 2H, CH₂), 3.40–3.53 (m, 4H, CH₂), 3.70 (t, 2H, CH₂), 7.83–8.12 (m, 4H, aromatic H), 8.25 (s, 3H, NH₃+), 9.18 (t, 1H, NH), 11.10 (s, 1H, NH) ppm.

The same method produces the compounds listed below in Table 12.

TABLE 12

| Ex. No. | Formula |
|---|---|
| 12.2 | HCl × H₂N–C₂H₄–NHCONH–CH₂–C₆H₄–SO₂–C₂H₄OH |
| 12.3 | HCl × H₂N–C₂H₄–NHCONH–C₂H₄–C₆H₄–SO₂–C₂H₄OH |

TABLE 12-continued
| Ex. No. | Formula |
|---|---|
| 12.4 | 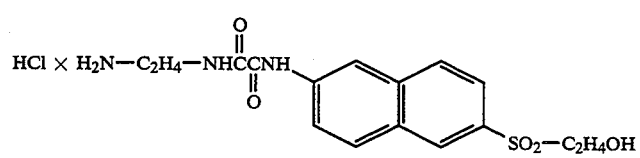 |
| 12.5 | 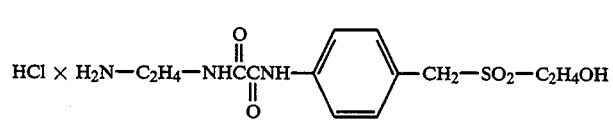 |
| 12.6 | 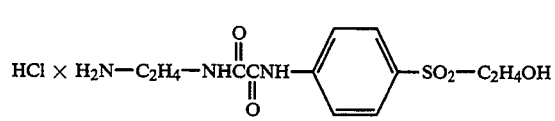 |
| 12.7 |  |
| 12.8 | 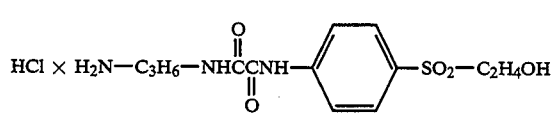 |
| 12.9 | 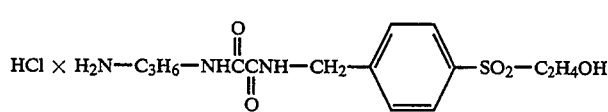 |
| 12.10 | 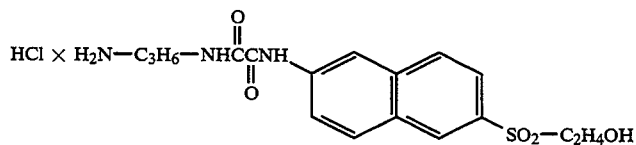 |
| 12.11 | 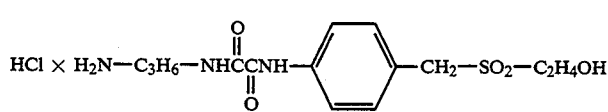 |
| 12.12 | 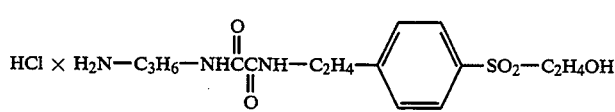 |
| 12.13 | 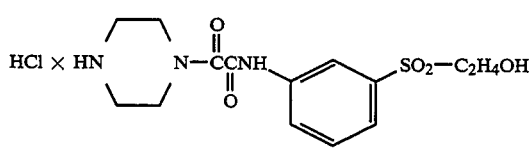 |
| 12.14 | 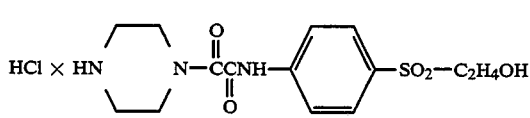 |
| 12.15 | 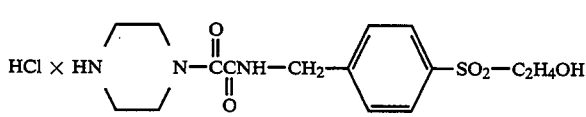 |

TABLE 12-continued

| Ex. No. | Formula |
|---|---|
| 12.16 | 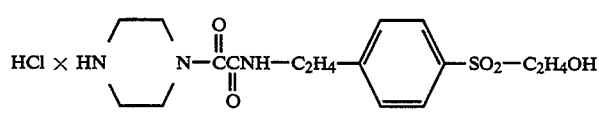 |
| 12.17 | 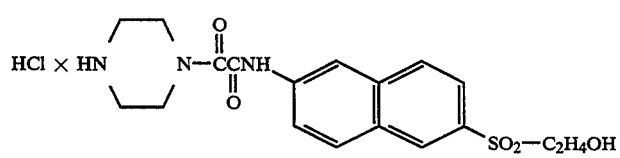 |
| 12.18 | 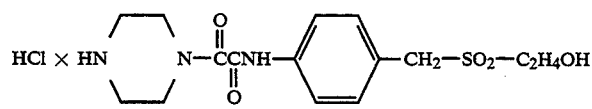 |

EXAMPLE 13.1

315 g (1 mol) of the compound described in Example 11.1 were introduced into 680 ml of concentrated sulfuric acid at 20°–30° C. and stirred at room temperature until the reaction had ended (TLC). The solution was discharged on to 900 g of ice, and the resulting precipitate was filtered off with suction and dried to leave 350 g of a compound of the formula

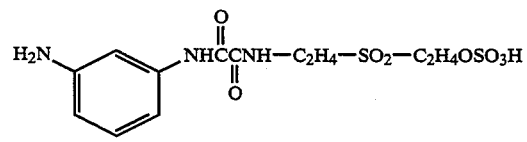

$^1$H NMR (d$_6$-DMSO); δ=3.40 (t, 2H, CH$_2$), 3.48 (t, 2H, CH$_2$), 3.70 (q, 2H, CH$_2$), 4.17 (t, 2H, CH$_2$), 7.12 (d, 1H, aromatic H), 7.48 (t, 1H, aromatic H), 7.78 (d, 1H, aromatic H), 8.03 (s, 1H, aromatic H), 9.10 (t, NH), 9.50 (s, 3H, NH$_3$+), 10.98 (s, 1H, NH) ppm.

The same method produces the compounds listed below in Table 13, although salting out may be necessary.

TABLE 13

| Ex. No. | Formula |
|---|---|
| 13.2 | 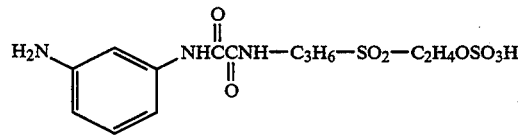 |
| 13.3 | 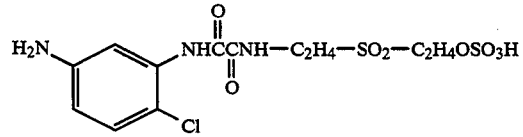 |
| 13.4 | 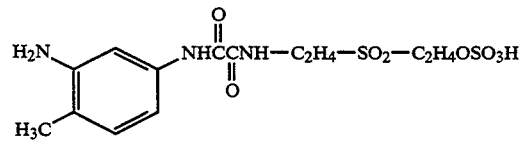 |
| 13.5 | 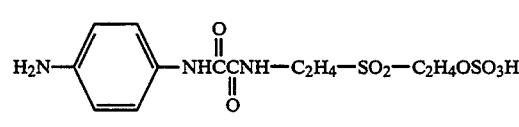 |
| 13.6 | 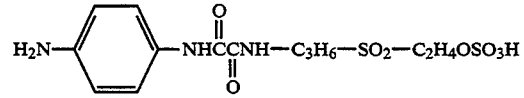 |

TABLE 13-continued
| Ex. No. | Formula |
|---|---|
| 13.7 | 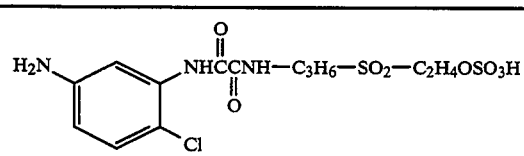 |
| 13.8 | 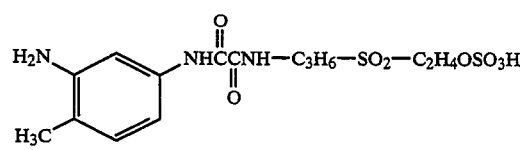 |
| 13.9 | 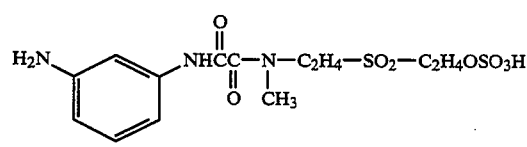 |
| 13.10 | 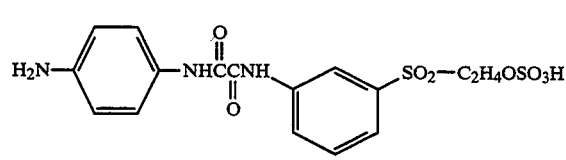 |
| 13.11 | 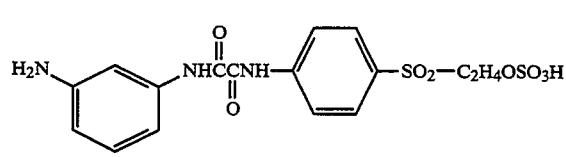 |
| 13.12 | 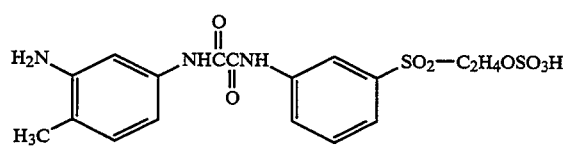 |
| 13.13 | 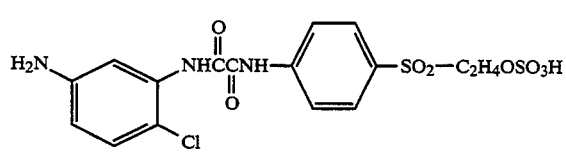 |
| 13.14 | 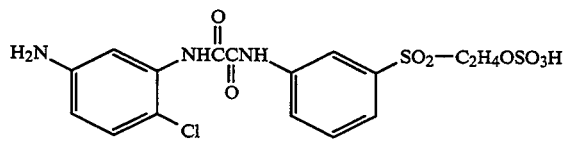 |
| 13.15 | 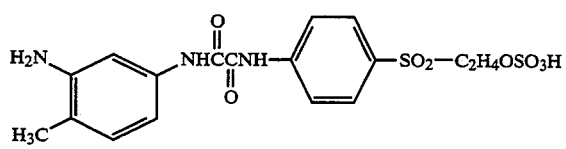 |
| 13.16 | 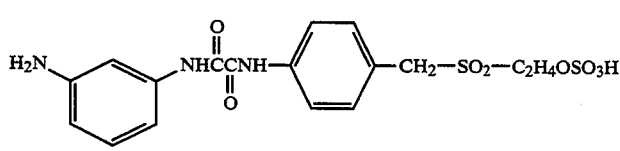 |

TABLE 13-continued

| Ex. No. | Formula |
|---|---|
| 13.17 | H₂N–C₆H₄–NHCONH–C₁₀H₅–SO₂–C₂H₄OSO₃H (3-amino-phenyl / 2,6-naphthalene) |
| 13.18 | H₂N–C₆H₄–NHCONH–C₁₀H₅–SO₂–C₂H₄OSO₃H (4-amino-phenyl / 2,6-naphthalene) |
| 13.19 | H₂N–C₆H₄(3)–NHCONH–CH₂–C₆H₄–SO₂–C₂H₄OSO₃H |
| 13.20 | H₂N–C₆H₄(4)–NHCONH–CH₂–C₆H₄–SO₂–C₂H₄OSO₃H |
| 13.21 | H₂N–C₆H₄(3)–NHCONH–C₂H₄–C₆H₄–SO₂–C₂H₄OSO₃H |
| 13.22 | H₂N–C₆H₄(4)–NHCONH–C₂H₄–C₆H₄–SO₂–C₂H₄OSO₃H |
| 13.23 | H₂N–C₂H₄–NHCONH–C₆H₄(1,3)–SO₂–C₂H₄OSO₃H |
| 13.24 | H₂N–C₂H₄–NHCONH–CH₂–C₆H₄–SO₂–C₂H₄OSO₃H |
| 13.25 | H₂N–C₂H₄–NHCONH–C₂H₄–C₆H₄–SO₂–C₂H₄OSO₃H |
| 13.26 | H₂N–C₂H₄–NHCONH–C₁₀H₅–SO₂–C₂H₄OSO₃H (2,6-naphthalene) |
| 13.27 | H₂N–C₂H₄–NHCONH–C₆H₄–CH₂–SO₂–C₂H₄OSO₃H |
| 13.28 | H₂N–C₃H₆–NHCONH–C₆H₄–SO₂–C₂H₄OSO₃H |

TABLE 13-continued
| Ex. No. | Formula |
|---------|---------|
| 13.29 | 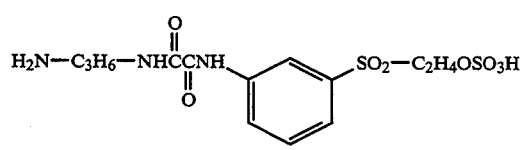 |
| 13.20 | 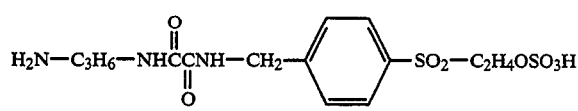 |
| 13.31 | 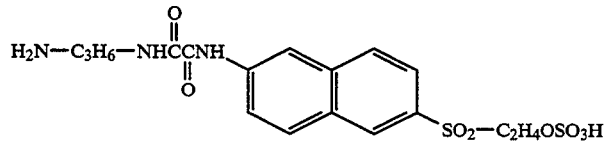 |
| 13.32 | 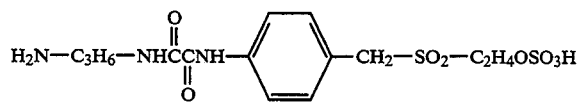 |
| 13.33 | 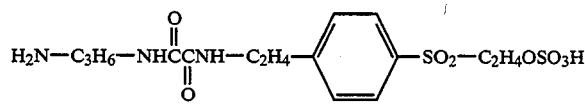 |
| 13.34 | 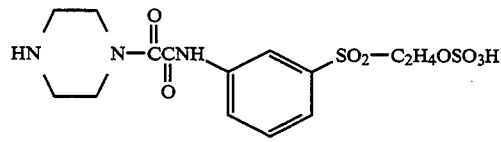 |
| 13.35 | 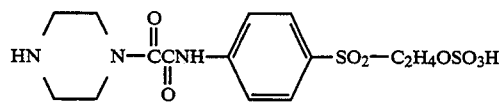 |
| 13.36 | 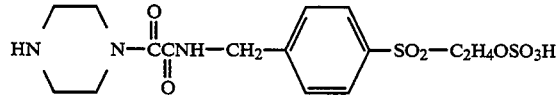 |
| 13.37 | 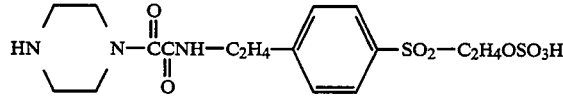 |
| 13.38 | 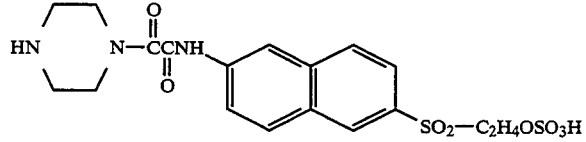 |
| 13.39 | 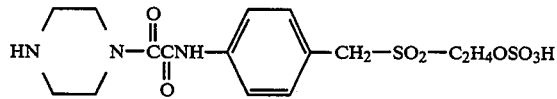 |
| 13.40 | 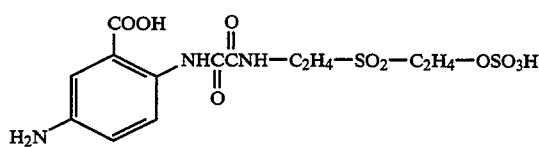 |

TABLE 13-continued

| Ex. No. | Formula |
|---|---|
| 13.41 | 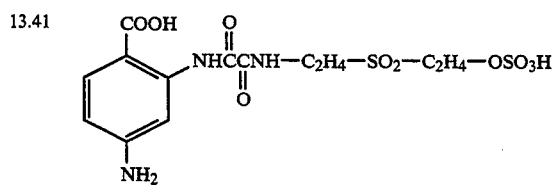 |
| 13.42 | 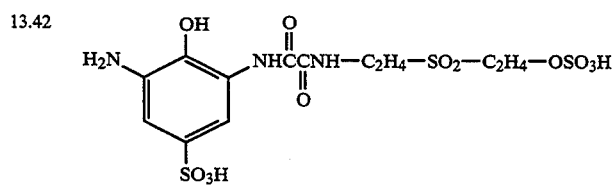 |
| 13.43 | 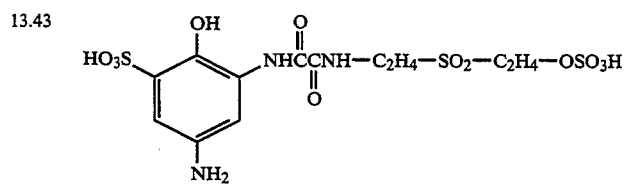 |
| 13.44 | 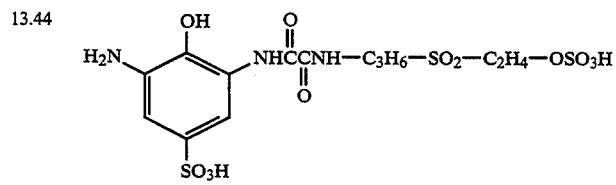 |
| 13.45 | 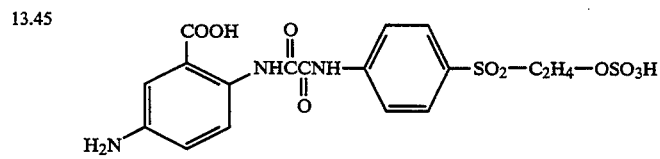 |
| 13.46 | 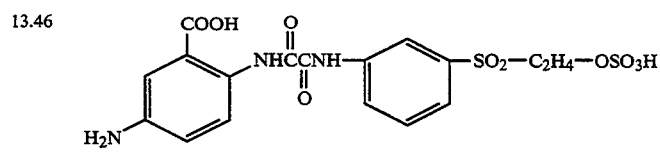 |
| 13.47 | 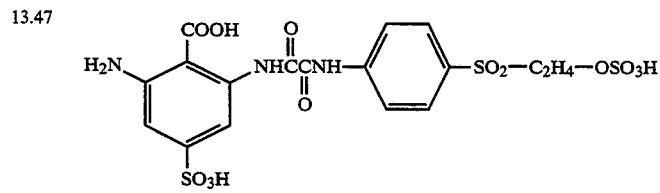 |
| 13.48 | 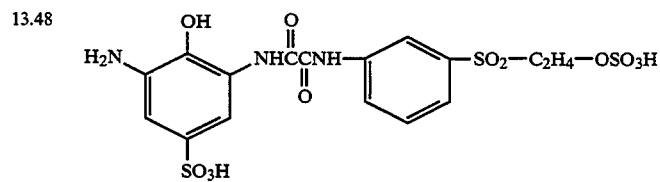 |

EXAMPLE 14.1

47 g (0.109 mol) of the compound described in Example 13.3 were suspended in 80 ml of water, adjusted with 2N sodium oxide solution to pH 10, and maintained at that pH and at room temperature until the elimination reaction had ended. The reaction mixture was then adjusted to pH 5 with 10% strength by weight hydrochloric acid, and the product was filtered off with suction and dried to leave 34.7 g of a compound of the formula

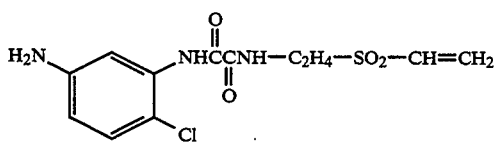

$^1$H NMR (d$_6$-DMSO); δ=3.38, (m, 2H, CH$_2$), 3.63 (m, 2H, CH$_2$), 5.50 (s, 2H, NH$_2$), 6.26–6.47 (m, 3H, CH=CH$_2$), 7.00–7.35 (m, 3H, aromatic H), 9.12 (t, 1H, NH), 9.87 (s, 1H, NH) ppm.

The same method produces the compounds listed in Table 14.

TABLE 14

| Ex. No. | Formula |
|---|---|
| 14.2 | H$_2$N—C$_6$H$_4$—NHCONHCONH—C$_2$H$_4$—SO$_2$—CH=CH$_2$ (3-amino) |
| 14.3 | H$_2$N, H$_3$C-substituted phenyl—NHCONHCONH—C$_2$H$_4$—SO$_2$—CH=CH$_2$ |
| 14.4 | H$_2$N—C$_6$H$_4$—NHCONHCONH—C$_3$H$_6$—SO$_2$—CH=CH$_2$ (3-amino) |
| 14.5 | H$_2$N, H$_3$C-substituted phenyl—NHCONHCONH—C$_3$H$_6$—SO$_2$—CH=CH$_2$ |
| 14.6 | H$_2$N, Cl-substituted phenyl—NHCONHCONH—C$_3$H$_6$—SO$_2$—CH=CH$_2$ |
| 14.7 | H$_2$N—C$_6$H$_4$—NHCONHCONH—C$_2$H$_4$—SO$_2$—CH=CH$_2$ (4-amino) |
| 14.8 | H$_2$N—C$_6$H$_4$—NHCONHCONH—C$_3$H$_6$—SO$_2$—CH=CH$_2$ (4-amino) |
| 14.9 | H$_2$N—C$_6$H$_4$—NHCOCON(CH$_3$)—C$_2$H$_4$—SO$_2$—CH=CH$_2$ (3-amino) |
| 14.10 | H$_2$N—C$_6$H$_4$—NHCONH—C$_6$H$_4$—SO$_2$—CH=CH$_2$ |
| 14.11 | H$_2$N—C$_6$H$_4$—NHCONH—C$_6$H$_4$—SO$_2$—CH=CH$_2$ |

TABLE 14-continued
| Ex. No. | Formula |
|---|---|
| 14.12 | 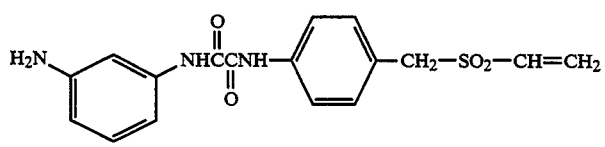 |
| 14.13 | 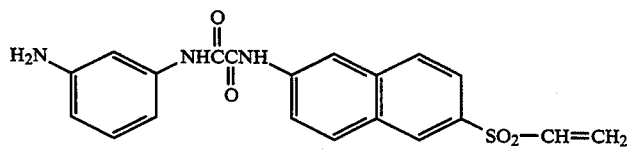 |
| 14.14 | 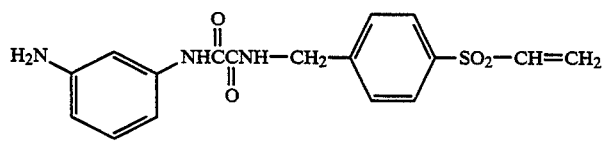 |
| 14.15 | 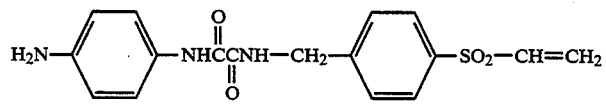 |
| 14.16 | 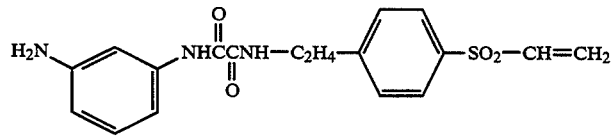 |
| 14.17 | 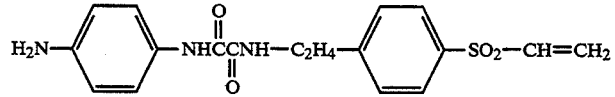 |
| 14.18 | 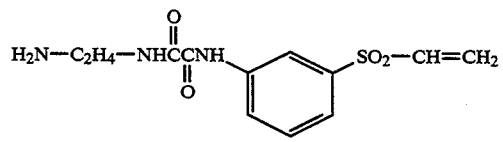 |
| 14.19 | 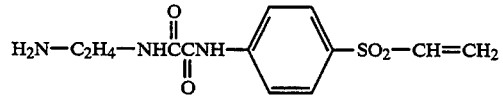 |
| 14.20 | 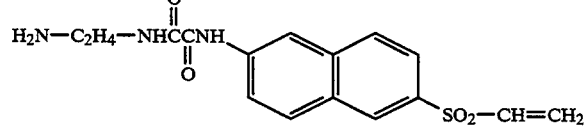 |
| 14.21 | 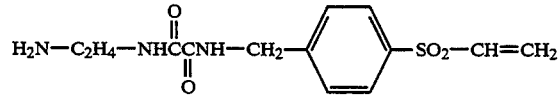 |
| 14.22 | 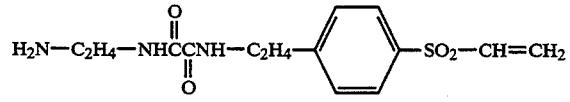 |
| 14.23 | 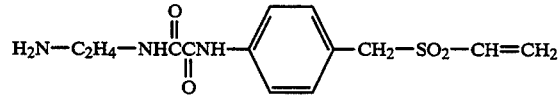 |

TABLE 14-continued
| Ex. No. | Formula |
|---|---|
| 14.24 | 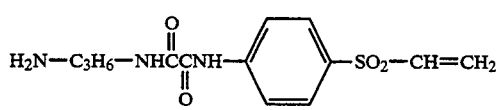 |
| 14.25 | 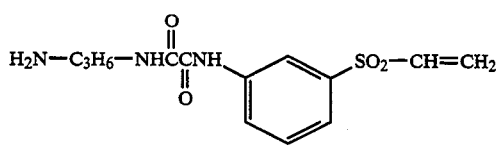 |
| 14.26 | 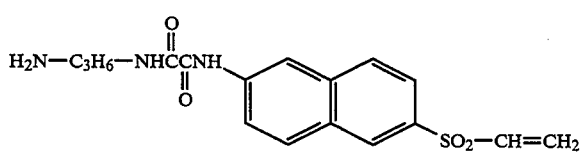 |
| 14.27 | 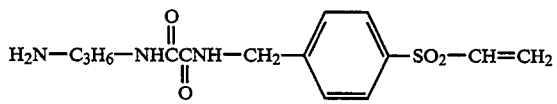 |
| 14.28 | 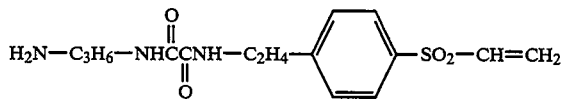 |
| 14.29 | 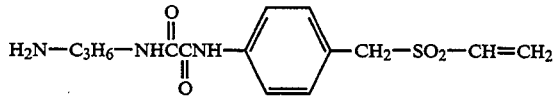 |
| 14.30 | 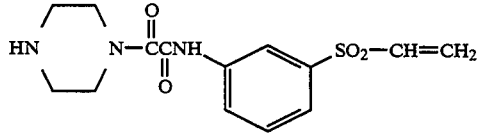 |
| 14.31 | 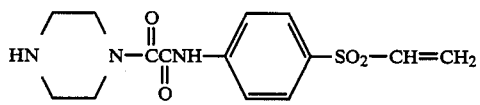 |
| 14.32 | 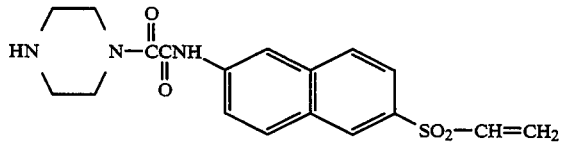 |
| 14.33 | 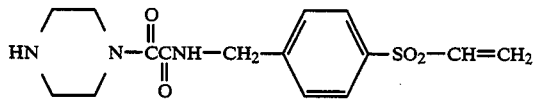 |
| 14.34 | 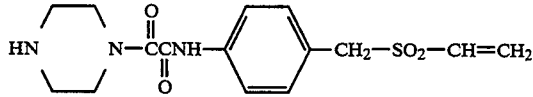 |
| 14.35 | 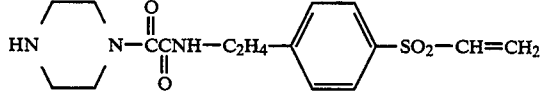 |

TABLE 14-continued

| Ex. No. | Formula |
|---|---|
| 14.36 | 2-COOH, 4-H₂N-phenyl-NHC(O)C(O)NH-C₂H₄-SO₂-CH=CH₂ |
| 14.37 | 3-H₂N, 2-OH, 5-SO₃H-phenyl-NHC(O)C(O)NH-C₂H₄-SO₂-CH=CH₂ |
| 14.38 | 3-H₂N, 2-OH, 5-SO₃H-phenyl-NHC(O)C(O)NH-C₃H₆-SO₂-CH=CH₂ |
| 14.39 | 2-COOH, 4-H₂N-phenyl-NHC(O)C(O)NH-(4-SO₂-CH=CH₂-phenyl) |
| 14.40 | 3-H₂N, 2-OH, 5-SO₃H-phenyl-NHC(O)C(O)NH-(4-SO₂-CH=CH₂-phenyl) |

EXAMPLE 15.1

To 1000 g of 23% strength by weight oleum were added at room temperature 16 g (0.04 mol) of the compound described in Example 13.1, and the mixture was stirred at room temperature for 20 hours. After the reaction had ended (TLC), the reaction mixture was discharged with ice-cooling on to 100 ml of saturated potassium chloride solution. The resulting precipitate was filtered off with suction, washed neutral with saturated potassium chloride solution and dried to leave 75 g of a solid which besides salt contained a compound of the formula 3-H₂N, 4-HO₃S-phenyl-NHC(O)C(O)NH-C₂H₄-SO₂-C₂H₄-OSO₃H $^1$H NMR (d$_6$-DMSO); δ=3.40 (t, 2H, CH$_2$), 3.48 (t, 2H, CH$_2$), 3.70 (q, 2H, CH$_2$), 4.17 (t, 2H, CH$_2$), 7.72–8.05 (m, 3H aromatic H), 9.17 (t, 1H, NH), 11.05 (s, 1H, NH) ppm.

The same method produces the compounds listed below in Table 15.

TABLE 15

| Ex. No. | Formula |
|---|---|
| 15.2 | 3-H₂N, 4-HO₃S-phenyl-NHC(O)C(O)NH-C₃H₆-SO₂-C₂H₄-OSO₃H |
| 15.3 | 3-H₂N, 5-SO₃H-phenyl-NHC(O)C(O)NH-C₂H₄-SO₂-C₂H₄-OSO₃H |
| 15.4 | 3-H₂N, 5-SO₃H-phenyl-NHC(O)C(O)NH-C₃H₆-SO₂-C₂H₄-OSO₃H |

EXAMPLE 16.1

52 g (0.15 mol) of the compound described in Example 3.11 were suspended in 200 ml of 1,4-dioxane, 10 g (0.165 mol) of ethanolamine were added, and the mixture was heated at 85° C. for 2 hours. After the reaction had ended (TLC), the mixture was cooled down, and the precipitate was filtered off with suction, washed with t-butyl methyl ether and dried to leave 40 g of a compound of the formula
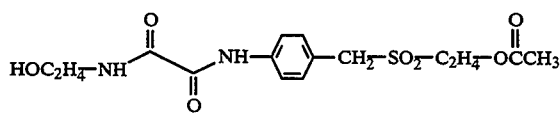
$^{13}$C NMR (d$_6$-DMSO), δ=20.5 (OCOCH$_3$), 42.0 (NCH$_2$), 50.5 (SO$_2$—CH$_2$—CH$_2$), 57.1 (CH$_3$COOCH$_2$), 58.9 (C$_6$H$_4$—CH$_2$—SO$_2$), 59.3 (CH$_2$OH), 120.4, 124.1, 131.1, 134.1, 137.8 (aromatic C) 158.6 (C$_6$H$_4$NHCO), 159.9 (NHCO), 169.9 (H$_3$C—CO)ppm.
The same method produces the compounds listed in Table 16.
TABLE 16
| Ex. No. | Formula |
|---|---|
| 16.2 | 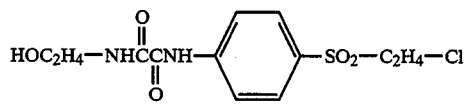 |
| 16.3 | 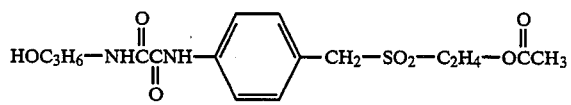 |
| 16.4 | 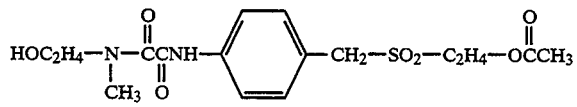 |
| 16.5 | 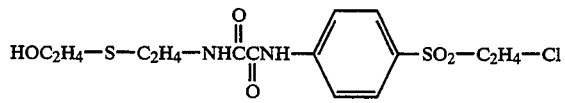 |
| 16.6 | 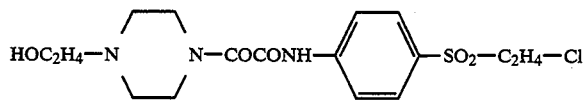 |
| 16.7 | 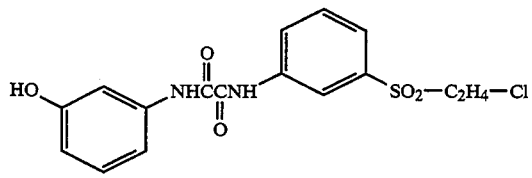 |
| 16.8 | 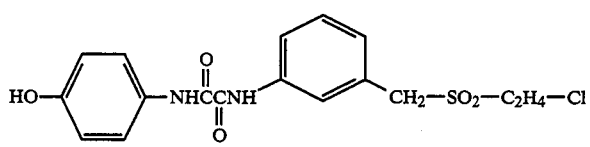 |
| 16.9 | 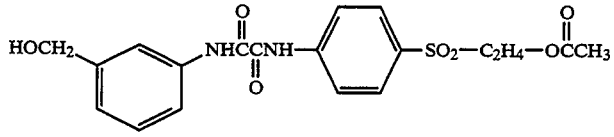 |
| 16.10 | 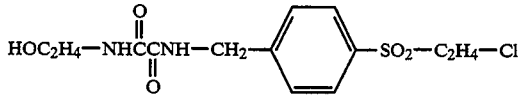 |
| 16.11 | 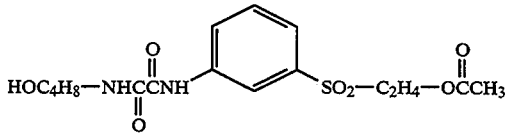 |
We claim:

1. Oxamides of the formula I

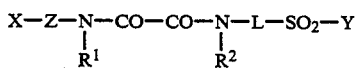

where
- $R^1$ and $R^2$ are independently of each other hydrogen, $C_1$-$C_4$-alkyl or phenyl,
- X is hydroxyl, nitro or a radical of the formula $-NR^3R^4$, where $R^3$ is hydrogen or $C_1$-$C_4$-alkanoyl and $R^4$ is hydrogen, $C_1$-$C_4$-alkyl or phenyl,
- Z is $C_2$-$C_8$-alkylene, substituted or unsubstituted phenylene or substituted or unsubstituted naphthylene, or X—Z and $R^1$ are, together with the nitrogen atom joining them together, the radical of the formula

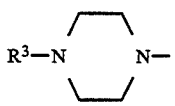

where
- $R^3$ is as defined above,
- L is $C_2$-$C_6$-alkylene, a radical of the formula

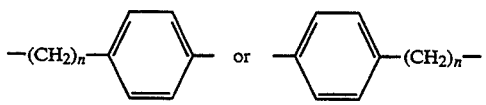

where
- n is 1 or 2, or substituted or unsubstituted phenylene or naphthylene, and
- Y is vinyl or a radical of the formula $-C_2H_4-A$, where A is hydroxyl or a group which is detachable under alkaline reaction conditions.

2. Oxamides as claimed in claim 1, wherein X is hydroxyl or amino.

3. Oxamides as claimed in claim 1, wherein Z and L are independently of one another phenylene or $C_2$-$C_6$-alkylene.

4. Oxamides as claimed in claim 1, where Y is vinyl or a radical of the formula $-C_2H_4-A$ where A is a group which is detachable under alkaline reaction conditions.

* * * * *

UNITED STATES PATENT AND TRADEMARK OFFICE
CERTIFICATE OF CORRECTION

PATENT NO. : 5,336,800
DATED : August 9, 1994
INVENTOR(S) : Bernd SIEGEL, et al.

It is certified that error appears in the above-indentified patent and that said Letters Patent is hereby corrected as shown below:

On the title page, Item [30], the Priority Number should be --4201699--

Signed and Sealed this

Eighth Day of November, 1994

Attest:

BRUCE LEHMAN

Attesting Officer     Commissioner of Patents and Trademarks